United States Patent
Shaw

(10) Patent No.: US 7,314,456 B2
(45) Date of Patent: Jan. 1, 2008

(54) SHOWER HEAD ATTACHMENT FOR CLEANING TEETH

(75) Inventor: Daniel A. Shaw, Naples, FL (US)

(73) Assignee: Health & Hygiene, Inc., Naples, FL (US)

( * ) Notice: Subject to any disclaimer, the term of this patent is extended or adjusted under 35 U.S.C. 154(b) by 56 days.

(21) Appl. No.: 11/238,614

(22) Filed: Sep. 29, 2005

(65) Prior Publication Data

US 2007/0073199 A1    Mar. 29, 2007

(51) Int. Cl.
*A61H 13/00* (2006.01)
(52) U.S. Cl. .................. 601/165; 601/160; 601/162; 433/80
(58) Field of Classification Search ............ 601/154, 601/155, 159, 160–163, 165, 169; 433/80, 433/89; 4/605, 606, 615
See application file for complete search history.

(56) References Cited

U.S. PATENT DOCUMENTS

| 4,043,337 A | | 8/1977 | Baugher |
| 4,265,229 A | | 5/1981 | Rice |
| 4,442,831 A | * | 4/1984 | Trenary ...................... 601/162 |
| 4,564,005 A | | 1/1986 | Marchand et al. |
| 4,793,331 A | | 12/1988 | Stewart |
| 4,991,569 A | * | 2/1991 | Martin ........................ 601/165 |
| 5,095,893 A | * | 3/1992 | Rawden, Jr. ................ 601/165 |
| 5,220,914 A | * | 6/1993 | Thompson ................... 601/155 |

* cited by examiner

*Primary Examiner*—Quang D. Thanh
(74) *Attorney, Agent, or Firm*—Allen D. Burfsky, PA

(57) ABSTRACT

A valve for adjusting the flow of water through an oral irrigation device connected to a shower head is located on a handle connected to a water-dispensing syringe or pick. Rotation of the valve controls the amount and pressure of water dispensed through the syringe or pick in a direct stream from the shower head.

2 Claims, 3 Drawing Sheets

SHOWER HEAD ATTACHMENT FOR CLEANING TEETH

BACKGROUND OF THE INVENTION

1. Field of the Invention

This invention relates to a dental hygiene device, and more particularly to a syringe for deliverying a stream of water for cleaning the teeth and gums of a user while showering.

2. Description of Prior Art

Numerous methods and apparatus have been suggested for cleaning the teeth and gums by using a jet stream of water.

One widely accepted system involves the use of a pulsating jet of water fed to a hand held syringe by an electrically driven pump placed beside a bathroom sink. This system requires a relatively expensive electrically driven pumping mechanism and the use of space adjacent the sink or water basin.

Therefore, it has been suggested that it would be less time consuming and less expensive to clean one's teeth and gums with a stream of water in a shower stall rather than over a sink. Different forms of apparatus designed to utilize an oral syringe in a shower are illustrated in U.S. Pat. Nos. 4,043,337; 4,265,229; 4,564,005; and 4,793,331. However, each of these systems requires a valve at the shower head to divert and redirect the stream of water through the syringe. For disabled persons in a wheelchair or for short people this is a distinct disadvantage negating their use of the device because they cannot reach the valve. Further, diverting the stream at the shower head results in stoppage of the shower flow altogether, so that while the stream is used for teeth or gum cleaning, it cannot be used as a body cleaning unit. These prior art devices are also not readily subject to disassembly to replace worn or inoperable parts. This invention overcomes these deficiencies of the prior art.

SUMMARY OF THE INVENTION

In accordance with the present invention, a valve for adjusting the flow of water through the device is located on the handle connected to the water-dispensing syringe or pick. Rotation of the valve controls the amount and pressure of water dispensed through the syringe or pick in a direct stream from the shower head. The valve and its components are threadedly connected between the syringe and handle of the device and can be readily disassembled to replace any worn parts.

BRIEF DESCRIPTION OF THE DRAWINGS

Further objects and advantages of the invention will become more apparent from the following description and claims and from the accompanying drawings, wherein:

DETAILED DESCRIPTION OF THE PREFERRED EMBODIMENT

Figure 1:
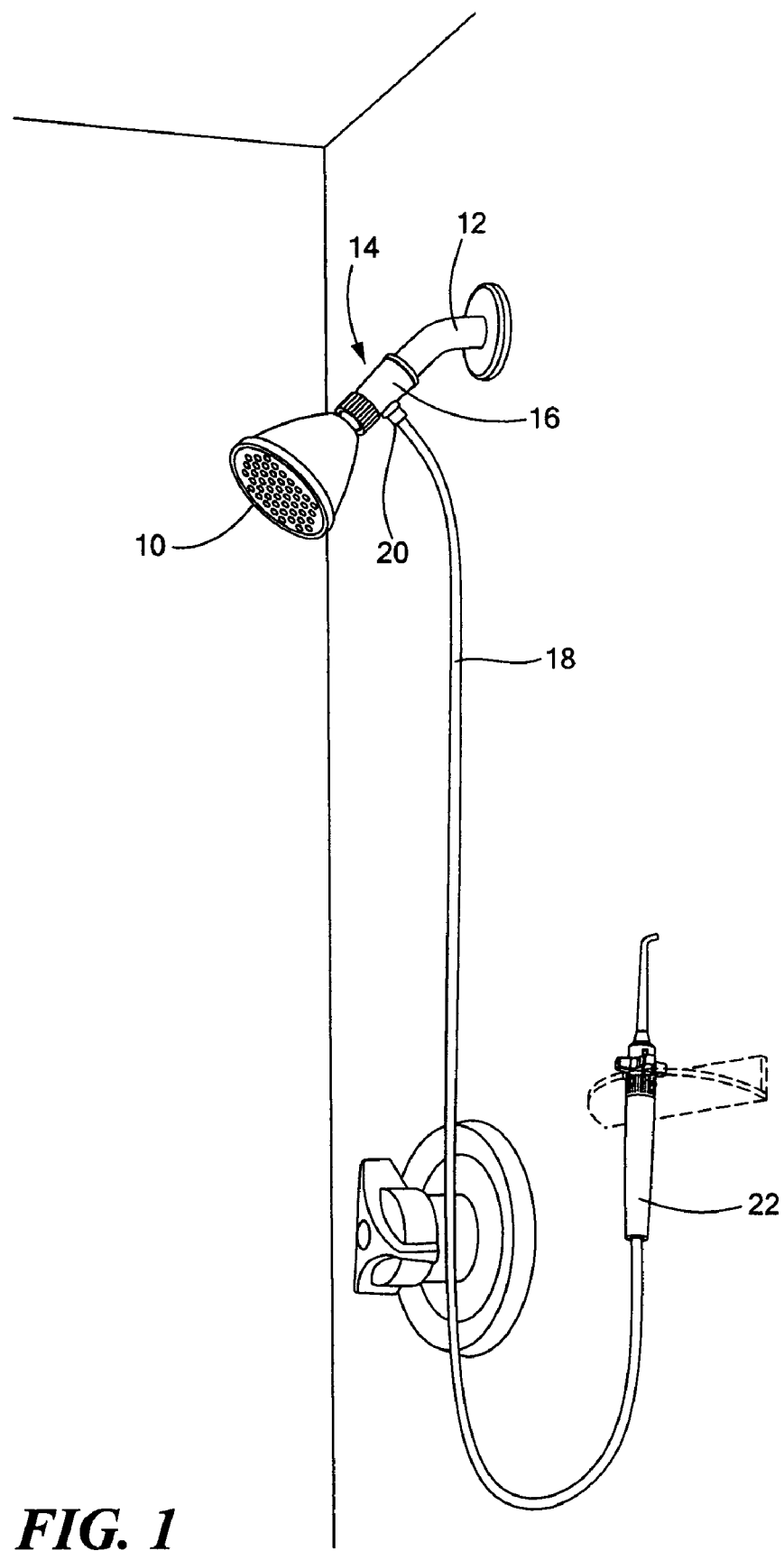
FIG. 1 is a fragmentary perspective view of a shower having the apparatus of the present invention attached thereto.
Figure 2:
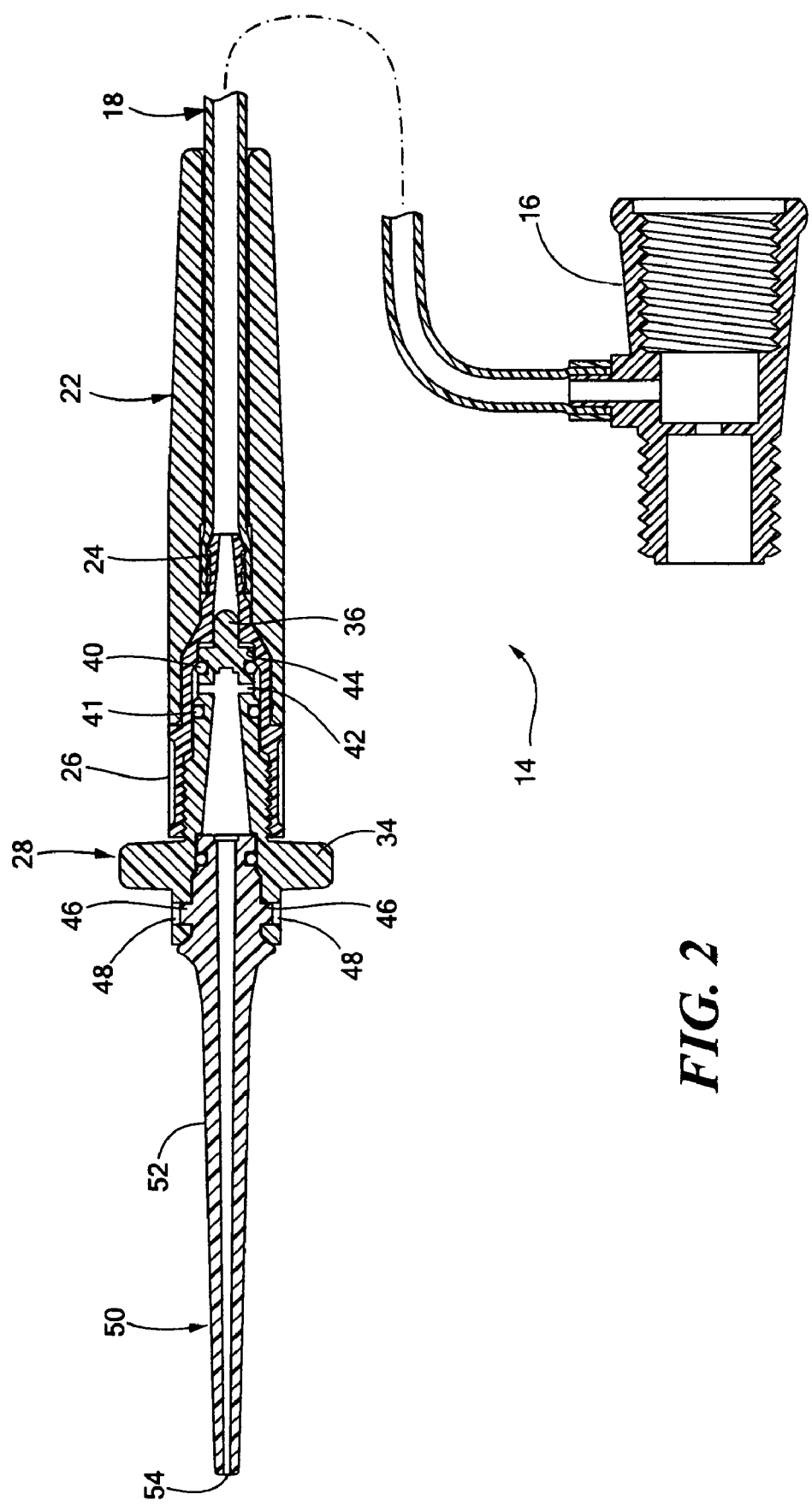
FIG. 2 is a longitudinal cross-sectional view of the apparatus of the present invention.
Figure 3:
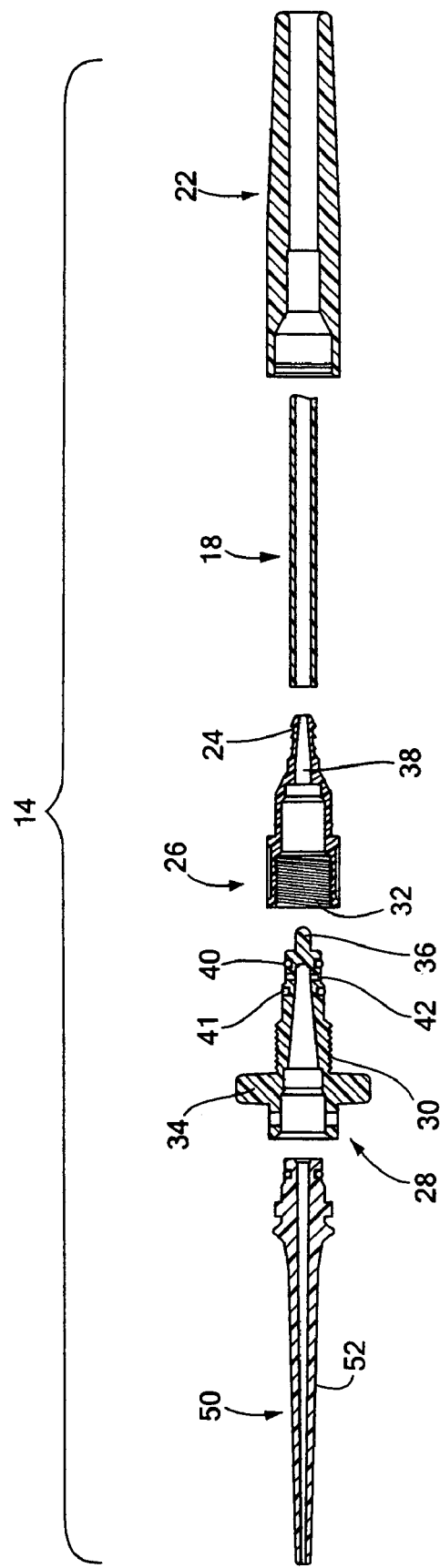
FIG. 3 is an exploded cross-sectional view of the components of the apparatus of the present invention, illustrating each of the components of the apparatus illustrated in FIG. 2 prior to their joinder.

Referring now to the drawings in detail, wherein like numerals indicate like elements throughout the several views, and in particular FIG. 1, a shower stall is illustrated which includes a conventional shower head 10, which receives water under pressure from inlet pipe 12. An oral irrigating assembly 14 in accordance with the present invention is interposed between shower head 10 and inlet pipe 12.

The assembly 14 includes a fixture 16 threadedly connected to inlet pipe 12 at one end and the shower head 10 at its opposite end. A flexible conduit 18 is fixed at one end to fixture 16, which has an opening 20 in communication with the interior of fixture 16. The distal end of flexible conduit 18 is received within the interior of a handle component 22 and connected over the serrated end 24 of a housing 26.

The housing 26 threadedly receives a valve 28 having a threaded cylindrical portion 30, received in threaded engagement with a complementary threaded portion 32 within housing 26. Rotation of threaded portion 30 by means of a handle 34 moves the valve element 28 linearly, relatively out of housing 26, while rotation in an opposite direction moves the valve linearly into the housing.

At the end of valve 28 is a nipple 36 which seats within the bore 38 of housing 26 and blocks the ingress of water from conduit 18 through the handle component 22. Rotation of the handle to open the valve, by moving it out of the housing, moves the nipple 36 out of bore 38. This enables water to enter the housing 26, flow around the nipple 36, past an O-ring seal 40 and against O-ring seal 41 on the valve and through an opening 42 into the interior of the housing. Depending on the distance of travel of the valve nipple 36 relative to the bore 38 of housing 26, the pressure and amount of the water delivered through opening 42 can be varied. Water at the same time, can still flow through the fixture 16 for body cleaning. To preclude the ingress of water from conduit 18 through valve 28, the valve handle is turned in an opposite direction until O-ring seal 40 seats on housing valve seat 44, effectively shutting the valve and precluding the ingress of water through the housing 26. In the event that nipple 36 becomes worn or truncated, leakage will be contained by O-ring seal 40.

Connected to valve 28 by a pair of oppositely extending projections 46 received in openings 48 on valve 28 is a syringe or water pick 50 having an elongated nozzle 52, provided with an opening 54. Water streaming through valve 28 emanating from shower head 10 is conducted through the interior of nozzle 52 against the teeth and/or gums of a user to clean the same.

It will be understood that the components of the apparatus are completely disassemble and the individual components as well as the O-ring seals may be replaced when worn as needed.

The invention claimed is:

1. A dental syringe for coupling between a water outlet and a showerhead, comprising:
    a fixture between said water outlet and showerhead for diverting water from said water outlet,
    a flexible conduit in fluid communication with said fixture through a first opening to receive diverted water from said water outlet,
    a handle component having a bore communicating with an opposite end of said flexible conduit through a second opening to receive the diverted water,
    a valve body received in an elongated housing disposed in said handle component, said housing having an end adjacent to the second opening in said flexible conduit, said valve body being provided with a rotatable handle portion and moveable linearly with respect to said housing upon rotation of said handle portion on said valve body, said valve body including means for precluding communication of said housing with the second opening in said flexible conduit upon rotation of said handle portion on said valve body in one direction, but enabling communication upon rotation of said handle portion on said valve body in an opposite direction, said means for precluding communication including a nipple on one end of said valve body seated in said housing adjacent said second opening in said flexible conduit to block ingress of diverted water from said conduit into said valve body upon rotation of said handle portion on said valve body in said one direction and to enable selective egress of diverted water from said bore upon rotation of said handle portion in said opposite direction moving said valve body in said housing away from said second opening in said flexible conduit, an oral irrigator coupled to said valve body for transmitting a jet of water to a user of the syringe upon rotation of said handle portion on said valve body in said opposite direction enabling communication between the second opening in said flexible conduit and said valve body, and wherein the end of said housing adjacent to the second opening in said flexible conduit in said handle component receiving and clamping the flexible conduit between said handle component and said housing to protect the nipple on said one end of said valve body.

2. The dental syringe of claim 1 wherein the end of said housing received in said flexible conduit is serrated.

* * * * *